US005523230A

United States Patent [19]

Smith

[11] Patent Number: 5,523,230
[45] Date of Patent: Jun. 4, 1996

[54] METHOD OF ENVIRONMENTAL CONTROL

[75] Inventor: Dale R. Smith, Rotorua, New Zealand

[73] Assignee: New Zealand Forest Research Institute Limited, Rotorua, New Zealand

[21] Appl. No.: 364,846

[22] Filed: Dec. 23, 1994

Related U.S. Application Data

[63] Continuation of Ser. No. 991,994, Dec. 17, 1992, abandoned.

[30] Foreign Application Priority Data

Dec. 18, 1991 [NZ] New Zealand .................. 241054

[51] Int. Cl.$^6$ ........................................... C12N 5/00
[52] U.S. Cl. .................. 435/240.45; 435/240.4; 435/240.49; 47/58

[58] Field of Search .................. 435/240.45, 240.4, 435/240.49, 284; 47/58, 66

[56] References Cited

U.S. PATENT DOCUMENTS 4,908,315  3/1990  Kertz ..................... 435/240.4
5,036,007  7/1991  Gupta ................... 435/240.45

Primary Examiner—Douglas W. Robinson
Assistant Examiner—Elizabeth F. McElwain
Attorney, Agent, or Firm—Abelman, Frayne & Schwab

[57] ABSTRACT

This invention is directed to a method for maturing plant material, such as cotyledonary stage embryos, on a medium which includes the step of placing a filter over a vessel containing the plant material and the medium, the filter being water vapor permeable and impermeable to microorganisms.

8 Claims, No Drawings

METHOD OF ENVIRONMENTAL CONTROL

This application is a continuation application under 37 C.F.R. 1.62 of prior application Ser. No. 07/991,994, filed on Dec. 17, 1992 now abandoned.

BACKGROUND TO THE INVENTION

This invention relates to a method of environmental control.

In particular, but not exclusively, this invention relates to a method of environmental control for plant material grown on solid medium. Reference throughout the specification will be made to the plant material as being somatic embryos, although it should be appreciated that the present invention can be applied to other plant material.

The growing of somatic embryos on a solid medium is still a relatively new science. Typically, the solid medium is a gelatinous/solid mixture with various ingredients such as minerals, sugars and amino acids which are required by the growing embryos. The medium in its liquid form is usually poured into containers such as Petri dishes. Once the medium has solidified, the embryos are placed onto the medium and the dish is covered with a plastic or glass lid or closure. The margins where the closure and dish overlap is sealed with a clear cling film. Cling film is used as it provides a seal against possible microbial infection which could be fatal to the embryos.

Cling film of the sort presently used is gas and vapor impermeable. While such cling film can effectively seal dishes against microbial infection, there are other problems associated with the use of this film.

One problem is that the use of vapour and gas impervious enclosure may result in build-up of condensation on the underside of the closure. This condensation not only causes viewing problems but it also causes more significant physiological problems: namely, condensate (generally water) may form which can drop back onto the medium. The medium has certain properties including a defined concentration of solutes which govern the rate at which water can be taken up by the growing embryos. It is important that the concentration of the various ingredients of the medium are at an optimum value for successful embryogenic development. Free water dropping onto the medium from the film can therefore cause the effective concentration of essential ingredients as received by the embryos to alter and can adversely affect the growth of the embryos.

There are believed to be additional problems to those described above caused by the use of traditional cling film.

While is was known in the past that fully developed plants have a gaseous exchange with the atmosphere, it was thought that this did not apply to plant embryos which were considered to be totally dependent on their internal environment. The basis of this belief was the understanding that embryos do not have a requirement for fixing carbon dioxide, as embryos do not photosynthesise unlike fully developed plants.

It is now believed by the applicant that embryos do have a gaseous exchange with the atmosphere. In the case of embryos grown under typical closure, there are strong indications that under the closure there is a build-up of ethylene and a possible depletion of carbon dioxide and oxygen. Ethylene is a bioactive substance and is thought to cause elongation of the cells in he embryos, perhaps to such an extent that the cells revert to non-embryogenic types. Auxins cause a similar undesirable effect on embryogenic tissues. The effect of the changing concentrations of oxygen and carbon dioxide is also thought to be harmful to the tissue.

It is an object of the present invention to address the above problems, or at least to provide the public with a useful choice.

Further objects and advantages of the present invention will become apparent from the following description which is given by way of example only.

SUMMARY OF THE INVENTION

According to one aspect of the present invention there is provided a method of growing plant material on a medium characterised by the step of placing a filter over a vessel containing the plant material and medium, said filter being gas and vapour permeable, and impermeable to microorganisms.

GENERAL DESCRIPTION OF THE INVENTION

Reference throughout this specification will now be made to the filter being a film, although it should be appreciated that other gas permeable filters may be used, for instance filters based on clay, charcoal and the like.

In preferred uses of the present invention, the plant material will be embryogenic in nature and the medium will be a solid medium, however it should be appreciated that the present invention could apply to situations different from those described herein, such as a liquid medium.

In a preferred embodiment, the film may be differentially permeable to the different gases and vapour such as oxygen, carbon dioxide, ethylene and water vapour. That is, the film may let through different gases and vapours at different rates to each other and therefore there can be provided a distinctive transmission ratio for these gases. Preferably, the transmission ratio for the gases and vapours through the film will correspond to the ratios of emission and absorption of the same gases by naturally growing plant material and in particular embryos if this is the material being grown.

In preferred embodiments of the present invention, the film allows a controlled rate of water loss. A preferred range of water loss for embryogenic tissue is between 90 to 150 grams/square meters/day. The unit grams refers to the weigh of the water, the unit square meters refers to the surface area of the culture medium being covered by the film. A preferred rate which is particularly suitable for *Pinus radiata* embryos is 118 grams/square meter/day.

In preferred embodiments, a filter which allows a controlled rate of exchange of oxygen is desired. In particular, it has been found that a range of between 7200 and 32000 cubic centimeters/square meters/day works particularly well. A optimum rate of oxygen exchange for *Pinus radiata* embryo has been found to be in the order of 16700 cubic centimeters/square meters/day.

Many types of film may be used for the present invention provided they have the desired qualities of being able to seal against microbial infection and are sufficiently permeable to the appropriate gases and vapours. For instance, the film may be made from plastics material such as polyvinyl chloride (PVC). Alternatively the film may achieve an appropriate filtering effect by being microporous with pores small enough to let gases through but not bacteria.

Table 1 on the following page illustrates properties of films which are suitable for use with the present invention. These films are sold under the trade mark VITAFILM® by the Goodyear Tire and Rubber Company (Australia) Limited. Of those films listed, the films listed under the names OMNI, VW, MWT and F10 V/S have provided the most promising results so far. In Particular, the OMNI film has shown itself to be particularly suitable for use in pine embryogenesis.

It should be appreciated that films and filters may be used other than the selection described above.

In a further aspect of the present invention, there is provided a method of growing plant material on a medium as described previously characterised by the further step of controlling the atmosphere outside of the film. For instance, a certain mixture of gases considered to be most suitable to the growth of embryogenic tissue may be supplied outside of the film ensuring that the growing embryos receive the appropriate mixture through the film.

of certain ingredients in the medium, and desiccation of the medium accompanied by maturation of the embryo including physiological changes that prepare it for desiccation.

Previously it was necessary to transfer the embryos from the lower concentration medium to the higher concentration medium to promote embryo development. Not only is this time consuming but it greatly increases the risk of damage and/or contamination of the embryogenic tissue. With the present invention, transference of tissue between media is now not necessary as the loss of water vapour through the permeable film naturally increases the concentration of ingredients in the medium sufficient to encourage embryo development. Simultaneous with this is an increase in the matrix potential—the ability of the medium to withhold water form the embryos during development. The progressive withholding of free water from the somatic embryos mimics the desiccation that occurs during natural embryo

| Property | Units | CW | Omni-film | PWGS | VW | MW | MWT | F10 V/S |
|---|---|---|---|---|---|---|---|---|
| Water vapour transmission rate | g m²/m²/24 hrs 95% rel hum 38° C. | 550 | 510 | 400 | 340 | 461 | 475 | 410 |
| Gas trans rate $O_2$ | cm³/m²/24 hrs | 15700 | 16700 | 8835 | 12300 | 14871 | 9500 | 7200 |
| Gas trans rate $O_2$ | cm³/m²/24 hrs | 14500 | 164300 | 63906 | 116200 | 168704 | 83000 | 62000 |
| Tensile strength longitudinal transverse | kg/cm² | 310 300 | 360 325 | 281 263 | 290 235 | 308 265 | 645 280 | 470 440 |
| Elongation longitudinal transverse | % | 270 335 | 250 275 | 270 350 | 250 275 | 224 276 | 180 450 | 250 280 |
| 100% modulus longitudinal transverse | kg/cm | 190 140 | 220 155 | 200 140 | 165 125 | 190 140 | 480 120 | 330 255 |
| Tear initiation (graves) longitudinal transverse | N/mm | 80 62 | 48 60 | 75 65 | 65 65 | 78 60 | 46 74 | 123 78 |
| Tear propogation (elemendorf) longitudinal transverse | N/mm | 25 45 | 12 26 | 24 45 | 25 45 | 25 44 | 25 44 | 12 26 |
| Drop height | Meters R.T | 1.4 | 1.1 | 1.2 | 1.8 | 1.2 | 1.8 | 1.0 |
| Sealing temperature | °C. | 150 | 160 | 150 | 172 | 150 | 165 | 150 |
| Flammability |  | Self extinguishing | Self extinguishing | Self extinguishing | Self extinguishing | Self extinguishing | Self extinguishing | Self extinguishing |
| Light transmission | % | 93 | 93 | 92 | 93 | 92 | 93 | 92 |
| Haze | % | 0.5 | 0.8 | 1 | 0.7 | 1 | 0.8 | 1 |
| Resistance to grease, oils, acids, alkalis |  | Good | Good | Good | Good | Good | Good | Good |
| Specific Gravity |  | 1.26 | 1.26 | 1.24 | 1.26 | 1.26 | 1.27 | 1.27 |

It can be seen that the present invention has a number of advantages over the methods previously used. As the film is permeable to water vapour, there is now no build-up of condensation. Thus, problems such as those relating to the changing concentration of minerals due to free water on the medium, have been avoided. As well, oxygen and carbon dioxide levels are now free to fluctuate in accordance with the physiological demands of the embryogenic tissue.

Further, with the present invention there is no build-up of ethylene with its potentially harmful effects on embryonic tissues. Accompanying the tissue multiplication stage in dishes with lids is an accumulation of fruity, volatile substances that are readily evident when a lid is removed. Included in this emission among other substances, is a build up of ethylene. However, with the present invention there is no detectable accumulation of fruity, volatile substances.

The present invention also provides an advantage beyond solving the problems previously discussed. The applicant has found that embryogenic tissue passes through two development stages.

The first development stage is the formation of the embryo axis which requires a lower concentration of certain ingredients in the medium.

The second development stage is the formation of the cotyledon primordia which requires a higher concentration development, and is achieved as a continuous process, rather than as a step-wise gradient such as would be obtained by serial transfer of tissue across media with different physical properties.

DETAILED DESCRIPTION OF THE INVENTION

Some examples whereby the use of the present invention are given below.

EXAMPLE 1

The effect of filters on pine somatic embryo production

Tissue of a plant forming *Pinus Radiata* embryogenic cell line was distributed in equal amounts at random over a number of petri dishes containing a solid medium that favours development and maturation of somatic embryos. Some of the dishes retained plastic lids which were sealed at the margins with impermeable cling film. Other dishes were covered with one of four different plastic films. After a period of ten days, cotyledonary stage embryos were harvested. The results are shown in Table 2 below. Each treatment had four dishes of embryo-forming tissue.

TABLE 2

| Film/Closure | Total number of somatic embryos |
|---|---|
| Plastic lid | 28 |
| Vitafilm F10 V/S* | 51 |
| Vitafilm VW* | 62 |
| Vitafilm Omni-film* | 97 |
| Vitafilm MWT* | 50 |

The use of Vitafilm Omni-film produced the greatest yield of somatic embryos.
*See previous Table 1 for film properties.

EXAMPLE 2

The determination of the affect of filters on water loss from growth medium in petri dishes.

Petri dishes containing solid somatic embryo development medium were covered with plastic lids, sealed on with cling film, or with one of four different gas permeable plastic films. Initial weights of the dishes were recorded, and weight loss noted at intervals of 2–3 days. There were four replicates of each treatment, and dishes were maintained in a 24° C. incubator under the same conditions as used for somatic embryo development.

The mean water loss from dishes after 9 days when covered with lids of different films was determined. Water loss was correlated with the somatic embryo counts from identical dishes of medium cultured under the same conditions. A correlation between embryo formation and water loss of 0.994 was determined statistically for the film covered dishes. Experimental results are shown in Table 3.

TABLE 3

Embryo formation and water loss from media

| Lid/Film | Number of Embryos | Water Loss (gm per 9 days) |
|---|---|---|
| Lid | 28 | 0 |
| Vitafilm F10 V/S | 51 | 4.88 |
| Vitafilm VW | 62 | 5.14 |
| Vitafilm Omni-film | 97 | 6.73 |
| Vitafilm MWT | 50 | 4.60 |

The water loss from dishes giving the highest yield of somatic embryos, that is those covered with Vitafilm Omni-film, was determined to be 118 $g/m^2$ dish area/day.

Aspects of the present invention have been described by way of example only and it should be appreciated that modifications and additions may be made thereto without departing from the scope of the appended claims.

I claim:

1. A method of maturing cotyledonary stage pine embryos on a medium, comprising (a) distributing embryogenic plant material onto a solid medium in a vessel, (b) placing a filter over the vessel containing the embryogenic plant material wherein said filter allows a controlled rate of water loss and a controlled rate of exchange of oxygen and is impermeable to microorganisms.

2. A method as claimed in claim 1 wherein said maturing cotyledonary stage pine embryos are *Pinus radiata* embryos.

3. A method as claimed in claim 1 wherein the filter is a film.

4. A method as claimed in claim 1 wherein the filter allows the transmission of water vapor at the rate of between 90 to 150 grams/square meter/day.

5. A method as claimed in claim 4 wherein the filter has a water vapor transmission rate of 118 grams/square meter/day.

6. A method as claimed in claim 4 wherein the filter allows oxygen to be exchanged at the rate of between 7200 and 32000 cubic centimeters/square meter/day.

7. A method as claimed in claim 6 wherein the filter allows the rate of oxygen exchange in the order of 16700 cubic centimeters/square meter/day.

8. A method of growing plant material on a medium as claimed in claim 1 and including the further step of controlling the atmosphere outside of the filer.

\* \* \* \* \*